United States Patent [19]

Bäthmann et al.

[11] 4,366,712
[45] Jan. 4, 1983

[54] ULTRASONIC TESTING OF SHEET AND PLATE STOCK

[75] Inventors: Hans-Jürgen Bäthmann, Moers; Gert Fischer, Mülheim; Heinz Schneider, Düsseldorf, all of Fed. Rep. of Germany

[73] Assignee: Mannesmann Aktiengesellschaft, Düsseldorf, Fed. Rep. of Germany

[21] Appl. No.: 185,565

[22] Filed: Sep. 9, 1980

[30] Foreign Application Priority Data

Sep. 7, 1979 [DE] Fed. Rep. of Germany ....... 2936737

[51] Int. Cl.³ ...................... G01N 29/00; G01N 29/04
[52] U.S. Cl. ....................................... 73/600; 73/599; 73/613
[58] Field of Search ................. 73/602, 600, 609, 610, 73/613, 618, 599

[56] References Cited

U.S. PATENT DOCUMENTS

| 3,572,099 | 3/1971 | Wieczorek | 73/602 |
|---|---|---|---|
| 3,780,570 | 12/1973 | Collins | 73/600 |
| 3,918,295 | 11/1975 | Herbertz | 73/613 |
| 3,952,578 | 4/1976 | Jacobs | 73/618 X |
| 4,041,774 | 7/1977 | Morris et al. | 73/610 |
| 4,173,897 | 11/1979 | Forsterman et al. | 73/609 |
| 4,173,898 | 11/1979 | Forsterman et al. | 73/612 |
| 4,201,093 | 5/1980 | Logon | 73/609 |
| 4,226,121 | 10/1980 | Knospler | 73/602 |
| 4,240,281 | 12/1980 | Lather et al. | 73/1 DV |
| 4,271,389 | 6/1981 | Jacobi et al. | 73/602 |

FOREIGN PATENT DOCUMENTS 2058350  4/1981  United Kingdom .................. 73/600

Primary Examiner—Edward R. Kazenske
Assistant Examiner—David V. Carlson
Attorney, Agent, or Firm—Ralf H. Siegemund

[57] ABSTRACT

Sheet or plate stock is used as to defects by a row of ultrasonic transmitting transducers on one side and receiving transducers on the other. The transmitting transducers receive frequency-modulated signals via individual buffers, and the receiving transducers feed individual, digital amplitude envelope minima to detection circuits whose outputs are fed to a computer which also feeds operating parameters to the source for the modulated signals. Different types (autonomy) of the receiver channels are described as well as diagnostic and setup procedures.

10 Claims, 2 Drawing Figures

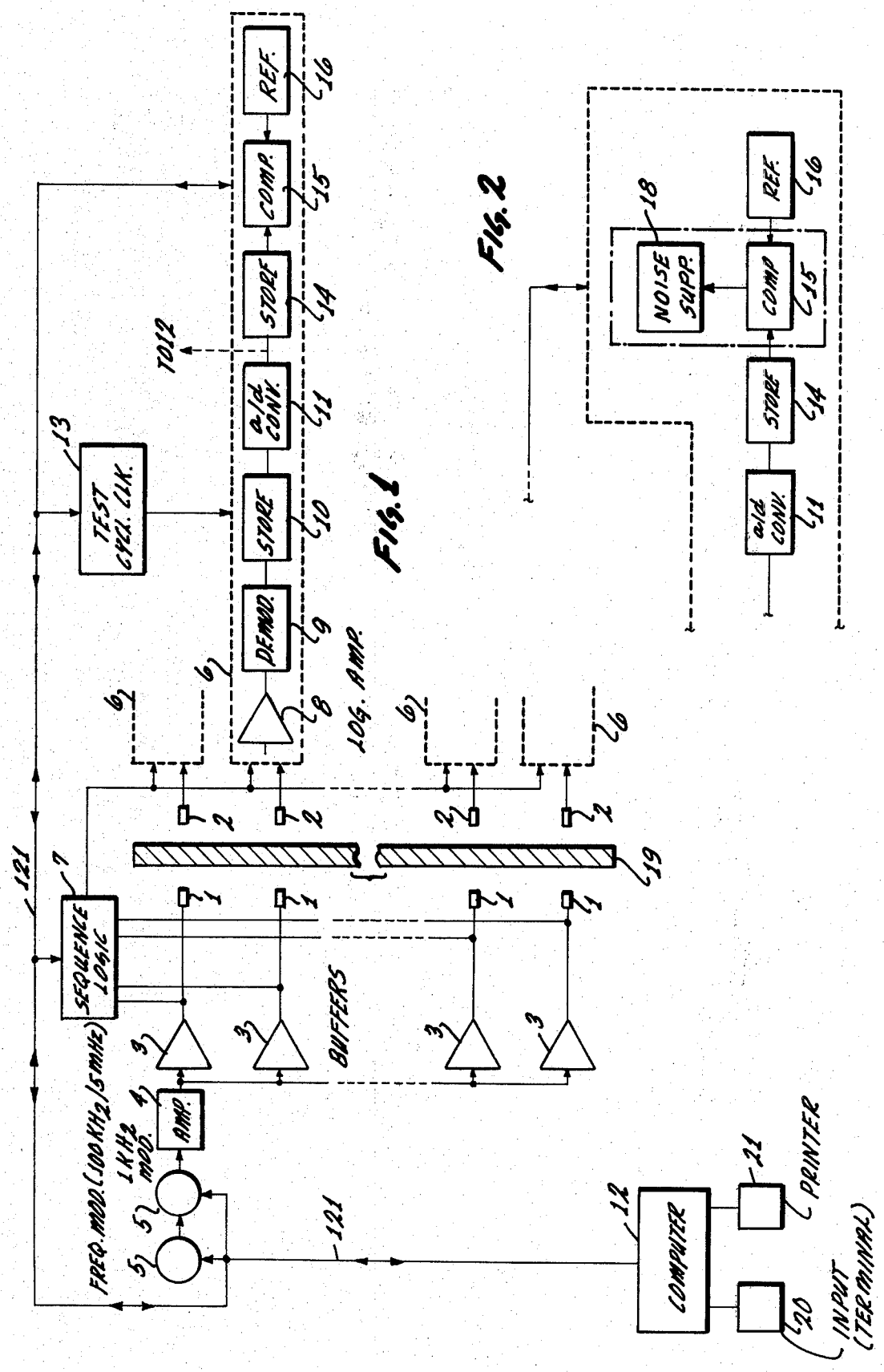

ULTRASONIC TESTING OF SHEET AND PLATE STOCK

BACKGROUND OF THE INVENTION

The present invention relates to ultrasonic testing of sheet metal or plates by means of continuous ultrasonic waves traversing the sheet or plate.

Metal sheets or plates are, for example, tested by means of utrasonic waves applied by a transmitting transducer which is coupled to the surface of the test object by means of water, such as a water jet. The ultrasonic wave traverses the material and is picked up at another location by means of a transducer which is also coupled to the test object by means of water. A plurality of transmitting transducers may be coupled to one side of a metal sheet or plate stock and receiving transducers to the other side.

By way of example, a transmitting transducer emits a cw beam of 2 megahertz. In order to avoid standing waves, this wave serves as a carrier and is modulated to have sidebands (shifts) of ±50 kHz and an additional frequency modulation of, e.g., 200 Hz. It was found, however, that frequently the resulting test sensitivity is not sufficient to fulfill present-day requirements in respect to flaw and defect detection.

Another problem is the following. The transmitting transducer is, for example, controlled via a passive network through which the energizing voltage is applied. Tolerances in electric properties of the transducer head, such as input impedance, resonance frequency, and so forth, produce certain mismatching conditions. In the case of a test device using a plurality of such heads (test channels), one obtains different sensitivities in the different channels. Particularly, one channel may recognize a defect that was missed by another one, so that an uncertainty is introduced into the overall evaluation, being based on processing of the various channels, and designed to verify defect detection.

Known ultrasonic testing devices include linear amplifiers for responding to the signals received by the receiving transducers of the system. These amplifiers are adjusted with respect to sensitivity without regard to an absolute level of sensitivity which the system as a whole may achieve. This may render individual ones of the test channels more sensitive to external interference because too high a sensitive system is prone to indicate defects where there is only "noise."

DESCRIPTION OF THE INVENTION

It is an object of the present invention to improve the ultrasonic testing of objects, in particular, of sheet or plate metal stock, using continuous waves rather than pulses.

In accordance with the preferred embodiment of the present invention, it is suggested to provide a frequency-modulated signal source connected to a plurality of transmitting transducers via channel-isolating buffer amplifiers; a plurality of receiving transducers are connected to receiving circuits, each including a logarithmic amplifier, a demodulation, an envelope minimum detector, and a digitizer for a detected minimum. A computing facility is provided to set the parameters of the source of frequency-modulated signals and to receive directly or indirectly the outputs of the digitizers. Indirect receiving is to mean that the individual receiving units already include some local digital processing, and the computer facility receives the result of that processing. The processing in the unit may include comparison of acquired minima values with a reference value, and either the difference or a logic statement about the sign of the difference is then transmitted to the computing facility. This way, the amount of information transmitted to the computing facility is reduced. A further reduction is possible if the local information in an individual receiving unit is statistically evaluated, to digitally filter comparative results and interpret spurious responses as noise.

DESCRIPTION OF THE DRAWINGS

While the specification concludes with claims, particularly pointing out and distinctly claiming the subject matter which is regarded as the invention, it is believed that the invention, the objects and features of the invention, and further objects, features, and advantages thereof, will be better understood from the following description taken in connection with the accompanying drawings, in which FIG. 1 is a block diagram of a system for practicing the preferred embodiment of the invention in accordance with the preferred mode thereof; and FIG. 2 is a block diagram for a supplemental system for the system of FIG. 1.

Proceeding now to the detailed description of the drawings, FIG. 1 illustrates sheet or plate stock 19 to be tested by means of ultrasonic test equipment. The test system includes a plurality of ultrasonic transmitting transducers 1 coupled by means of water to one side of the stock 19, while receiving transducers 2 are disposed adjacent to and along the opposite side, in respective alignment with the transmitting transducers 1 of the plurality. One transmitting transducer 1 and the respectively oppositely located receiving transducer 2 constitute the principal components of a test channel. The receiving transducers are also acoustically coupled to the sheet by means of water. In each instance, a free water jet may be employed. The transducers may be arranged to cover, as groups, the entire width of the sheets or plates, passing through the testing station in a direction transverse to the plane of the drawings of FIG. 1.

As far as the transmitter circuit and system is concerned, it includes two programmable signal generators 5, producing a frequency-modulated transmitter voltage. The two generators 5 are cascaded, the first one may produce a subcarrier-type modulation of 100 kHz on a 5 MHz carrier (frequency shift by ±100 kHz), while the second generator provides a modulation of, e.g., 1 kHz, set directly into a signal line that feeds a power amplifier 4.

These two generators are digitally controlled by a computing facility 12 which adjusts particularly the amplitude, the center frequency (carrier), frequency fluctuation (subcarrier modulation) or shift and modulation frequency. These parameters may be adjusted individually for each testing task, even for each channel and transmitting transducer. Raising the center frequency from 2 MHz to 5 MHz may produce a significant increase in test sensitivity.

As stated, signal generators 5 are adjusted by the computer 12 as to their output parameters. The computer 12 controls also other functions and serves particularly as an acquisition unit for the multichannel test results. The unit 12 is mainly a processor with memory facility to which are connected peripheral equipment devices. One of them being the pair of generators 5. The connection is made via an I/O bus 121. Another output device is a printer 21 to print the test result, e.g., on a running basis as the sheet or plate stock passes through. Reference numeral 20 refers to an input device, e.g., a terminal by means of which an operator communicates with the processor and, for example, sets up the unit for testing and runs it through different modes.

As stated, the combined output of signal generators 5 is applied to the power amplifier 4 which, in turn, feeds all of a plurality of buffer amplifiers 3. The primary function of the buffers 3 is to decouple electrically the test channels from each other. Individual test head tolerances or even malfunctions thereof do not interfere with the operation of the other channels, particularly the respective adjacent ones. Low output impedances of the buffers 3 permit optimizing the power match thereof to the individual transducers 1.

The receiving transducers 2 are individually connected to individual receiver units 6. A receiver unit 6 is comprised of a logarithmic amplifier 8 because a large, dynamic range has to be covered by the system. The amplifier feeds an amplitude demodulator 9 feeding its output to a store 10 for the minimum value of the demodulated amplitude as received. The output of this circuit 10 is fed to an analog-to-digital converter 11. A clock unit 13 determines the test cycle rate. Detection of a signal amplitude minimum by unit 10 may be limited to a cycle and at the end of each test cycle, the lowest amplitude value acquired during that cycle is digitized. The value, thus provided, is fed to the computer 12 via the common bus 121, to be accummulated therein and processed for the detection of flaws, their orientation, extension, and verification. A defect may be defined by an increase in acoustic impedance of the sheet metal or scattering by a fault, or the like, so that the detected amplitude drops. The determination of an undue amplitude drop may be made by the computer 12 for each channel and for each test cycle.

The output of converter 11 may be fed alternatively to a channel-dedicated digital store 14 to be locally compared with a reference value. That reference value is, e.g., updated by the computer 12; but a specific value was initially set into the reference store 16. Reference numeral 15 denotes a comparator which compares the value stored in digital store 14 towards the end of a test cycle with that reference value as a first, local flaw detection step. Minimum circuit 10 may provide a new value per modulation cycle, and device 14 stores the lowest amplitude value per test cycle. The output of the digital comparator may be a simple true/false statement, or the difference value itself. In this case, the computer will be evaluating the locally detected difference signal between stored reference and acquired minimum amplitude. It is up to the computer to determine the significance, such as, for example, of just ignoring any difference in which the acquired amplitude is above the reference. A true/false indicator may suffice for that purpose and may be furnished by the comparator 15 to the computer instead. A false indication may signal a higher acquired amplitude, and the computer may ignore these indications and respond only to true indications.

The illustrated system includes another circuit or subsystem, centered in a control logic 7. All output terminals of transmitter channel buffers 3 can feed their inputs to the logic 7 to be selected one by one. The respective signal can be sent into the evaluating units 6 as alternative inputs. Thus, this circuit bypasses the transducers 1 and 2. This subsystem will be called upon by the computer in a diagnostic mode, wherein a diagnostic program attempts to localize a circuit or other system defect.

Another mode was already briefly mentioned above. For setup, e.g., under utilization of a standard "sheet" as test object, one may acquire data from which reference values are deduced, to be set into the stores 16 in the various channels. These reference values may be different for different channels to offset any channel tolerances. In a system without local units 14, 15, and 16, such reference values may be markers on the printout sheet, or values stored in the computer to be used by a program for comparing purposes.

The setup procedure includes also the determination of the requisite parameters for the modulation signal sources 5, ultimately to adjust the sensitivity of the system to the expected noise level. This then includes also selection and adjustment of the carrier and modulation frequencies. Increasing the carrier frequency, for example, from 2 MHz to 5 MHz increases the test sensitivity. Selection of a most suitable value can be made, e.g., on a trial-and error basis since the computer (via the input terminal) can readily be used to determine response levels (e.g., outputs of digitizers 11) for different carrier and/or modulation frequencies.

FIG. 2 illustrates a modification for further limiting the amount of information that must pass from the individual units 6 to the computer. The output of the comparator 15, e.g., a sequence of true/false signals, is fed to a statistical evaluation device 18 which suppresses spurious responses and permits only, e.g., persisting "true" responses to be passed on to the computer. Conceivably, device 14 may provide an updated minimum value once per modulation cycle, being shorter than a test cycle, and the statistical evaluation takes place throughout a test cycle. If desired, a statistical evaluation may cover more than one test cycle.

In operation, the sheet or plate stock 19 passes through the test equipment, and the various transducers 1 issue ultrasonic waves being modulated as described. These waves are passed on to the test object 19 via water coupling; they pass through the test object and will reach predominantly the respectively oppositely located receiving transducer 2. The resulting electrical signals in transducers 2 are amplified in the respective logarithmic amplifier 8 and demodulated.

Due to the frequency modulation, the ultrasonic waves may receive an amplitude modulation upon passage through the metal. Depending upon the texture and other properties of the stock, the ultrasonic waves are attenuated to some extent, resulting in a "normal" level, including a minimum in the amplitude envelope per modulation cycle. That minimum may drop in case a fault, inclusion, or the like, scatters or otherwise attenuates the passing-through waves further. The respective amplitude minimum on each modulation cycle is detected by analog circuit 10 and digitized in converter 11.

Depending upon the degree of sophistication and autonomie of each evaluation channels 6, the outputs of digitizer 11 may be sequentially fed directly to the computer 12 and on command of the test cycle unit 13. In this case, units 14, 15, 16, and 18 do not have to be provided for. Alternatively, the digitized minimum may be set into the digital storage unit 14 to be compared with the reference value held in unit 16. As stated, unit 10 may be provided in this case to detect the amplitude envelope minimum for each modulation cycle, and unit 14 detects the lowest amplitude per test cycle. The comparison between the amplitude minimum as acquired and the reference is made in unit 15, and its output, being a digital difference signal or a true/false signal, is called up by the test cycle unit 13 and fed to the computer 12.

In the modification of FIG. 2, the statistical unit 18 responds to a sequence of difference signals as provided persuant to sequential modulation cycles or test cycles by the comparator 15, to suppress spurious responses, representing an unlikely event. As to different test cycles, a true defect will exhibit a gradual approach of the amplitude minima to the reference value as stored in unit 16; then, and only then, will unit 18 issue, e.g., a true signal being indicative that the detected minima have dropped below the reference. From a different point of view, sequential modulation cycles may have their respective amplitude envelope minima not only detected, but used in units 14-15; and for each test cycle, a statistical evaluation is made whether or not the number of "true" signals exceeds a prescribed minimum. Then, and only then, will an indication be made to the computer.

It can readily be seen that the statistical approach reduces the amount of data issued by the units 6 to the computer. This is an important saving, particularly in the case of a large number of test channels.

Test cycles may include also a selection of individual transmitting transducers under utilization of one or more receiving transducers. In this case, individual parameters may be set into the source 5. Also, not selected transmitting transducers may be decoupled.

We claim:

1. Apparatus for ultrasonic testing of sheet or plate metal stock, comprising:
a plurality of ultrasonic transmitting transducers positioned for being disposed on one side of the stock to be tested;
a plurality of ultrasonic receiving transducers disposed on an opposite side of said stock for receiving ultrasonic signals that have passed therethrough;
a plurality of buffer amplifiers, having their respective outputs connected respectively to the plurality of transmitting transducers;
a source for frequency-modulated electrical signals connected for driving the buffer amplifiers;
a plurality of receiving circuit units connected respectively to the receiving transducers, each receiving circuit including a logarithmic amplifier, an amplitude demodulator, a minimum detector and store for storing detected demodulation minima, and a digitizer for the stored minima; and
a computing facility connected to said source to provide thereto operating parameters and further connected to said digitizers to produce test results.

2. Apparatus as in claim 1 and including means, operated by the computing facility to connect the outputs of the buffer amplifiers to said receiving circuits, bypassing the transducers, for purposes of diagnostics.

3. Apparatus as in claim 1 and including a test cycle clock operating said digitizer for producing one digitized minimum per test cycle.

4. Apparatus as in claim 1 or 3, wherein the digitizers feed outputs directly to said computing facility.

5. Apparatus as in claim 1 or 3, each receiving circuit including means for comparing a respective output of the digitizer of the circuit with a reference, and providing to said computing facility a result indicative of the comparison.

6. Apparatus as in claim 5, said means for comparing including a source of reference signals, the computing facility being connected to said source of reference signal to provide thereto the reference signal.

7. Apparatus for ultrasonic testing of sheet or plate metal stock, comprising:
a plurality of ultrasonic transmitting transducers positioned for being disposed on one side of the stock to be tested;
a plurality of ultrasonic receiving transducers disposed on an opposite side of said stock;
a plurality of buffer amplifiers, having their respective outputs connected respectively to the plurality of transmitting transducers;
a source for frequency-modulated electrical signals connected for driving the buffer amplifiers;
a plurality of receiving circuits including minimum amplitude detection means, a digitizer and local processing means as well as logic decision-making means to evaluate the signals as received and providing true/false indicators; and
a computing facility connected to all of said receiving circuits to receive therefrom said true/false indications, to obtain a representation of absence or presence of defects in the stock.

8. Apparatus as in claim 7, said computing facility further connected to provide operating parameters to said source to adjust and preset the test sensitivities.

9. Apparatus as in claim 1 or 7, each receiving circuit including means for statistically reprocessing the digitizer output.

10. Apparatus as in claim 9 each receiving circuit including means for comparing a respective output of the digitizer of the circuit with a reference, and providing to said computing facility a result indicative of the comparison.

* * * * *